United States Patent [19]

Orlek et al.

[11] Patent Number: 4,870,081
[45] Date of Patent: Sep. 26, 1989

[54] AZA-BICYCLIC COMPOUNDS

[75] Inventors: Barry S. Orlek; Michael S. Hadley; Harry J. Wadsworth, all of Harlow; Howard E. Rosenberg, Barnet, all of England

[73] Assignee: Beecham Group p.l.c., Brentford, England

[21] Appl. No.: 67,364

[22] Filed: Jun. 26, 1987

[30] Foreign Application Priority Data

Jun. 27, 1986 [GB] United Kingdom ............... 8615785

[51] Int. Cl.⁴ ................... C07D 221/22; A61K 31/45
[52] U.S. Cl. .................... 514/299; 514/216; 514/413; 546/112; 546/183; 540/581; 548/453
[58] Field of Search .............. 546/112, 183; 540/581; 548/453; 514/216, 299, 413

[56] References Cited

U.S. PATENT DOCUMENTS

| | | | |
|---|---|---|---|
| 2,658,067 | 11/1953 | Duschinsky | 546/137 |
| 3,501,471 | 3/1970 | Remers et al. | 544/234 |
| 3,681,363 | 8/1972 | Elkin et al. | 546/18 |
| 4,038,402 | 7/1977 | Kaminka et al. | 514/305 |
| 4,203,990 | 5/1980 | Yen | 546/133 |

FOREIGN PATENT DOCUMENTS

| | | | |
|---|---|---|---|
| 14193/83 | 5/1983 | Australia . | |
| 0094742 | 11/1983 | European Pat. Off. | 546/112 |
| 0239309 | 9/1987 | European Pat. Off. . | |
| 1470084 | 3/1969 | Fed. Rep. of Germany | 546/112 |
| 047681 | 9/1978 | Japan | 546/112 |
| 2019588 | 7/1985 | Japan | 546/112 |

OTHER PUBLICATIONS

Home Medical Encyclopedia, vol. 1, p. 158.
Brian Richardson et al., CA 104:19506g.
H. S. Aaron et al., *J. Amer. Chem. Soc.*, 89, pp. 1431-1437 (1967).
G. Lambrecht and E. Mutschler, *Drug Res.*, 24, p. 1725 (1974).
C. A. Grob and E. Renk, *Helv. Chim. Acta.*, 37, p. 1689 (1954).
M. J. Martell and T. O. Soine, *J. Pharm. Sci.*, 52, pp. 331-336 (1963).

M. D. Mashkovsky, *Proc. 1st Int. Pharmacol. Meet.*, 7, p. 359 (1963).
D. Spry and H. S. Aaron, *J. Org. Chem.*, 84, pp. 3674-3676 (1969).
L. H. Sternbach and S. Kaiser, *J. Amer. Chem. Soc.*, 74, pp. 2219-2221 (1952) ("Sternbach-I").
L. H. Sternbach and S. Kaiser, *J. Amer. Chem. Soc.*, 74, pp. 2215-2218 (1952) ("Sternbach-II").

*Primary Examiner*—Jane T. Fan
*Attorney, Agent, or Firm*—James F. Haley, Jr.; Teresa L. Solomon; David K. Barr

[57] ABSTRACT

A compound of formula (I) or a pharmaceutically acceptable salt thereof:

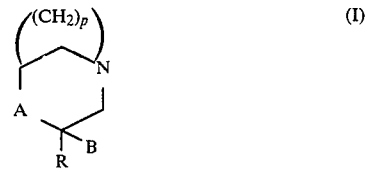

in which A represents a bond or —CH$_2$— and B represents hydrogen, or A and B together with the carbon atom to which they are both attached represents a group

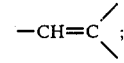

R represents R$_1$OOC— in which R$_1$ is C$_{1-4}$ alkyl, C$_{2-4}$ alkenyl or C$_{2-4}$ alkynyl; R$_2$O— in which R$_2$ is C$_{1-3}$ alkyl, C$_{1-2}$ alkylcarbonyl or aminocarbonyl optionally substituted by one or two methyl groups; or R$_3$CH$_2$— in which R$_3$ is C$_{1-2}$ alkoxy; and p represents an integer of 2 to 4, and wherein compounds of formula (I) where B is hydrogen have the stereochemical configuration in which the group R and the methylene bridge are both on the same side of the plane of the molecule which contains both bridge head atoms and the ring carbon atom bonded to the group R.

7 Claims, No Drawings

AZA-BICYCLIC COMPOUNDS

This invention relates to compounds having pharmaceutical activity, to a process for their preparation and their use as pharmaceuticals.

3-Acetoxyquinuclidine, commonly known as aceclidine, is known to possess a strong cholinomimetic action (M. D. Mashkovsky, Proc. 1st. Int. Pharmacol. Meet. 7, 359 (1963)). The higher esters such as propionyl and butyryl and optionally di-N-methyl substituted carbamates are known to possess little or no cholinomimetic activity.

A group of compounds has now been discovered which enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

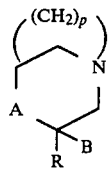

in which A represents a bond or —CH$_2$— and B represents hydrogen, or A and B together with the carbon atom to which they are both attached represents a group

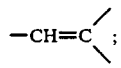

R represents R$_1$OOC— in which R$_1$ is C$_{1-4}$ alkyl, C$_{2-4}$ alkenyl or C$_{2-4}$ alkynyl; R$_2$O— in which R$_2$ is C$_{1-3}$ alkyl, C$_{1-2}$ alkylcarbonyl or aminocarbonyl optionally substituted by one or two methyl groups; or R$_3$CH$_2$— in which R$_3$ is C$_{1-2}$ alkoxy; and p represents an integer of 2 to 4.

It will be understood that the compounds of formula (I) where B is hydrogen have the stereochemical configuration in which the group R and the methylene bridge are both on the same side of the plane of the molecule which contains both bridge head atoms and the ring carbon atom bonded to the group R. This configuration will hereinafter be referred to as the exo configuration.

Certain compounds of formula (I) are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferably A represents a bond or —CH$_2$— and B represents hydrogen.

Preferably, p represents 2 or 3.

Examples of alkyl moieties in R include methyl, ethyl, n- or iso-propyl, and n-, iso, sec- or tert-butyl. Preferably alkyl moieties in R are methyl or ethyl.

Alkenyl or alkynyl moieties in R preferably have 3 carbon atoms, for example propargyl.

Suitable examples of R include methoxycarbonyl, ethoxycarbonyl, prop-2-ynyloxycarbonyl, methoxy, ethoxy, n-propoxy, methylcarbonyloxy, ethylcarbonyloxy, aminocarbonyloxy, methylaminocarbonyloxy, dimethylaminocarbonyloxy and methoxymethyl.

The invention also provides a process for the preparation of a compound of formula (I), or a pharmaceutically acceptable salt thereof, which process comprises:

(a) cyclising a compound of formula (II):

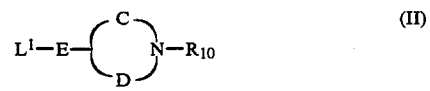

where R$_{10}$ is hydrogen or an N-protecting group, and either C is one, D is another and E is the remainder of —(CH$_2$)$_p$—, —CH$_2$— and

or groups conveertible thereto and L$^1$ is a leaving group, or C is one and E is the other of —(CH$_2$)$_p$— and —(CH$_2$)— or groups convertible thereto and D represents

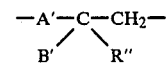

where A' and B' represent A and B or groups convertible thereto and R″ and L$^1$ together represent —COO—, and thereafter, optionally or as necessary and in any appropriate order, converting C, D and E to —(CH$_2$)$_p$—, —CH$_2$— and

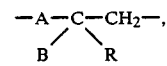

removing any R$_{10}$ protecting group, interconverting R and/or forming a pharmaceutically acceptable salt, or (b) cyclising a compound of formula (III):

where F is one and G is the other of —(CH$_2$)$_p$— and —CH$_2$— or groups convertible thereto, and one of X and Y is —(CH$_2$)$_m$—W and the other is —(CH$_2$)$_n$-(CO)$_q$L$^2$ where W is an electron withdrawing group, L$^2$ is a leaving group, m is 1 or 2, n is 0 or 1 and q is 0 or 1, with the proviso that, when Y is —(CH$_2$)$_n$-

$(CO)_QL^2$, n and q are each 1, and thereafter, optionally or as necessary and in any appropriate order, hydrolysing and decarboxylating the cyclisation product and converting the carbonyl group to CHR' where R' is R or a group convertible thereto, or, where X is —COL² and Y is —(CH₂)₂W, reducing the carbonyl group in the cyclisation product to hydroxy and dehydrating the resulting alcohol, converting W to R' as defined, converting R' to R, converting F and G to —(CH₂)ₚ— and —CH₂— as appropriate, interconverting R and/or forming a pharmaceutically acceptable salt, with the proviso that m, n and q are such that the desired compound of formula (I) is obtained.

Examples of leaving groups L¹ include halo, such as chloro, and hydroxy. Examples of L² include those given for L¹ or, when q is 1, C₁₋₄ alkoxy such as ethoxy. Examples of electron withdrawing groups W include C₁₋₄ alkoxycarbonyl and cyano. An example of a group convertible to

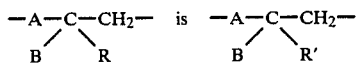

where R' is a group convertible to R, such as hydroxy.

In the intermediates of formulae (II) and (III), preferably A is a bond or CH₂ and B is hydrogen.

In the process variant (a), where L¹ is hydroxy and D is —CHOH—CH₂—, the cyclisation may be carried out by pyrolysis, by the method of D. O. Spry and H. S. Aaron, J. Org. Chem., 1969, 34, 3674, to yield a compound where R' is hydroxy.

Where L¹ and R'' together represent —COO—, the cyclisation is a rearrangement reaction which can be carried out under acid conditions in a polar solvent, such as hydrogen bromide in ethanol, at ambient temperature, to yield a compound where R' is a carboxylic ester group. It is preferred to protect the nitrogen atom with an R₁₀ N-protecting group such as benzyl, which may be subsequently removed by hydrogenation over a suitable catalyst such as Pd/C.

In the process variant (b), where X and Y both contain carboxylic ester groups, the cyclisation is a Dieckmann reaction which is catalysed by a base such as potassium t-butoxide at elevated temperature in a solvent such as toluene.

The resulting β-keto ester is hydrolysed and decarboxylated under conventional conditions such as heating at reflux in dilute hydrochloric acid.

The carbonyl group may then be reduced to an R' hydroxy group with a suitable reducing agent such as sodium in ethanol at elevated temperature, such as the boiling point of the solvent, under an inert atmosphere such as nitrogen. Alternatively, the carbonyl group may be converted to an R' cyano group with a suitable reagent such as tosylmethylisocyanide in an inert solvent such as dry dimethoxyethane, at depressed temperature, under basic conditions such as the presence of potassium t-butoxide.

Where q is 0, the cyclisation may be carried out as described in EP-0094742 under basic conditions such as sodium hydride and potassium t-butoxide, in an inert polar solvent such as dimethyl formamide.

Where X is —COL², Y is —(CH₂)₂W, F is —(CH₂)ₚ— and G is —CH₂—, the cyclisation product is of the formula (IIIa):

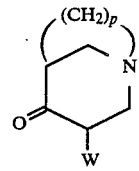

which may be reduced by conventional procedures with an alkali metal borohydride such as sodium borohydride in a lower alcohol such as ethanol, to yield the 4-hydroxycompound which may be dehydrated under conventional conditions for the formation of an unsaturated system, such as under strongly acidic conditions e.g. with concentrated sulphuric acid and glacial acetic acid, at elevated temperature such as the boiling point of the solvent, the acid reagent optionally acting as the solvent.

The nature of the conversions of the groups W and R', and interconversions of R, will depend upon the required group R. Thus, where R is R₂O—, an R' hydroxy group may be converted:

(i) where R₂ is alkyl, by etherification under conventional conditions, for example by reaction of the alcoholate anion (formed under basic conditions e.g. with sodium hydride) with a compound R₂X¹ where X¹ is a leaving group as halo e.g. bromo or iodo, in an inert solvent such as dimethylformamide, at ambient to elevated temperature. It may be necessary to protect the nitrogen atom with a suitable protecting group such as benzyl during the etherification, the group being subsequently removable by hydrogenation over a suitable catalyst such as Pd/C;

(ii) where R₂ is C₁₋₂ alkylcarbonyl, by esterification under conventional conditions with the acid R₂OH or suitable derivative thereof e.g. the acid anhydride, in a polar solvent such as dimethylformamide, or the acid or derivative itself acting as the solvent, at elevated temperature such as the boiling point of the solvent;

(iii) where R₂ is optionally substituted aminocarbonyl, by haloformylation with a suitable haloformate ester such as phenylhaloformate e.g. phenyl chloroformate, under basic conditions e.g. in the presence of pyridine, at depressed temperature, followed by nucleophilic substitution with the appropriate substituted amine in an inert solvent or the amine itself acting as the solvent, at ambient temperature.

Where R is R₁OOC, an R' or W cyano group may be hydrolysed to the intermediate acid under acidic conditions e.g. hydrochloric acid at elevated temperature. The acid may be esterified by reaction with the appropriate alcohol R₁OH under acidic conditions at elevated temperature, to give the compound of formula (I).

Where R is R₃CH₂—, an R' or W —COOH or R₁OOC— group may be reduced to the primary alcohol (R'=—CH₂OH) with a suitable reducing agent such as LiAlH₄ in an inert solvent such as tetrahydrofuran. This alcohol may be etherified to give a compound where R₃ is alkoxy, by a procedure analogous to that described at (i) above.

Interconversion of R groups may be carried out conventionally. Thus, for example, alkylcarbonyloxy or aminocarbonyloxy groups may be converted to the alcohol by acid or base hydrolysis, while alkoxycarbonyl groups may be converted to the free acid by acid or base hydrolysis, then further converted as described above for R'.

In another aspect, a process for preparing compounds of formula (I) comprises:

(c) converting a compound of formula (IV):

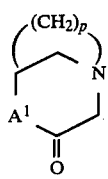

in which $A^1$ represents a bond or —$CH_2$— and p is as defined in formula (I), into a compound of formula (IVa):

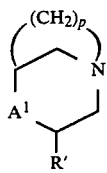

in which R' is R as defined in formula (I) or a group convertible thereto; or (d) dehydrating a compound of formula (V):

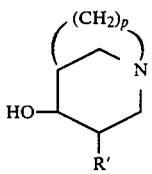

in which p is as defined in formula (I) and R' is as defined in formula (IVa), to give a compound of formula (Va):

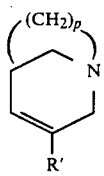

and thereafter, optionally or as necessary, converting R' to R, converting R to other R and/or forming a pharmaceutically acceptable salt.

The conversion and dehydration steps are as described above.

Intermediates of formulae (II), (III) (IV) and (V) are known compounds or may be prepared analogously to known compounds.

Intermediates of formula (II) where R" and $L^1$ together represent —COO— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

Intermediates of formula (II) where $L^1$ is a leaving group are described in, for example, Spry et al., J. Org. Chem., 1969, 34, 3674 and Hasse et al., Chem. Ber., 1960, 93, 1986.

Intermediates of formulae (III) and (IV) are described in, for example, Martell et al., J. Pharm. Sci., 1963, 52(4), 331, Sternbach et al., J.A.C.S., 1952, 74, 2215, Thill et al., J. Org. Chem., 1968, 33, 4376 and EP-0 094 742.

The intermediate of formula (V) where p is 3 and R' is —$CO_2C_2H_5$ is described in J. Amer. Chem. Soc 45, 2738 (1923).

Intermediates of formula (VI):

wherein the variables are as defined in formula (I), and salts thereof also form part of the invention.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions. In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

In another aspect, the invention provides the use of a compound of formula (1) or a pharmaceutically acceptable salt thereof in the manufacture of a medicament for the treatment and/or prophylaxis of dementia in mammals including humans.

The dose of the compound used in the treatment of such disorders will vary in the usual way with the seriousness of the disorders, the weight of the sufferer, and the relative efficacy, of the compound. However, as a general guide suitable unit doses may be 0.05 to 100 mg, for example 0.2 to 50 mg; and such unit doses may be administered more than once a day, for example two or three times a day, so that the total daily dosage is in the range of about 0.01 to 10 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

The following examples illustrate the invention and the following descriptions illustrate the preparation of intermediates thereto.

Description 1

(±) exo-1-Azabicyclo[3.3.1]nonan-3-ol

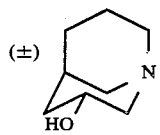

(D1)

A solution of 1-azabicyclo[3.3.1]nonan-3-one* (6.5 g; 0.047 mole) in ethanol (120 ml) was heated at reflux under nitrogen and sodium (15.4 g, 0.67 mole) added in small portions over 2.5 h. After the addition was complete the reaction mixture was heated under reflux until all the metal had dissolved. The solution was cooled in an ice bath, diluted with saturated sodium chloride solution (30 ml) and the pH adjusted to 11 with conc. HCl. The mixture was extracted with chloroform (4×100 ml). The combined organic extracts were dried (Na$_2$SO$_4$) and concentrated in vacuo to give the title compound as an orange oil (7.7 g crude), which was used without further purification.

*M. J. Martell Jnr. and T. O. Soine, J. Pharm. Sci., 1963, 52 (4), 331 (ref. 1)

Nmr (CDCl$_3$): δ: 1.40–2.20 (7H, m, 3×CH$_2$, CH) 2.70–3.30 (6H, m, 3×CH$_2$N) 4.00–4.40 (1H, m, CHOH)

Description 2

(±) exo-3-Cyano-1-azabicyclo[3.3.1]nonane

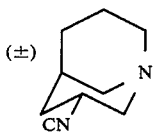

(D2)

A solution of 1-azabicyclo[3.3.1]nonan-3-one* (4.7 g, 0.034 mole) and tosylmethylisocyanide (7.2 g, 0.037 mole) in dry dimethoxyethane (150 ml) at 0° C. was treated with ethanol (3 ml) followed by the portionwise addition of potassium tert-butoxide (8.3 g, 0.075 mole) over 0.5 h. The mixture was stirred at 0° C. for a further 1 h and then at room temperaturefor 20 h. The mixture was treated with water (25 ml), then saturated by adding solid potassium carbonate and extracted with ethyl acetate. The organic extract was dried (K$_2$CO$_3$), filtered and concentrated in vacuo to leave a dark red oil. This was chromatographed on silica gel eluting initially with chloroform, increasing to 8% methanol/chloroform to give the title compound as a red oil (2.64 g, 52%).

* ref. 1

Nmr (CDCl$_3$) δ: 1.30–2.40 (7H, m, 3×CH$_2$, CH) 2.80–3.50 (7H, m, 3×CH$_2$N, CHCN) IR ν (CN) 2225 cm$^{-1}$

Description 3

(±) exo-6-Cyano-1-azabicyclo[3.2.1]octane

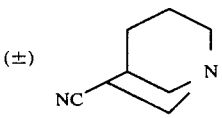

(D3)

1-Azabicyclo[3.2.1]octan-6-one* (3 g, 0.024 moles) in dry, 1,2-dimethoxyethane (100 ml), under nitrogen, was treated with tosylmethyl isocyanide (7 g, 0.036 moles) and ethanol (1.8 g) at 0° C. Potassium t-butoxide (6.8 g, 0.06 moles) was added portionwise at such a rate as to be able to maintain the temperature below 5° C. The reaction mixture was allowed to warm to room temperature over 30 min., and then heated at 40° C. for a further 30 min. The mixture was cooled and filtered and the residue washed with dimethoxyethane. The combined filtrates were concentrated in vacuo and the residual gum separated by column chromatography on alumina eluting with methanol (3%–10%)/ethyl acetate into exo and endo isomers. The faster running exo isomer was distilled in a Kugelrohr b.p. 130°/0.1 mm Hg to give 1.0 g of a colourless oil.

*L. H. Sternbach and S. Kaiser, J.A.C.S., 1952, 74, 2215 (ref. 2)

Ir $\nu$ (CN) 2225 cm$^{-1}$

Description 4

(±) Ethyl 4-hydroxy-1-azabicyclo[3.3.1]non-3-yl carboxylate

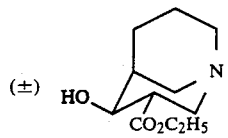

(D4)

A solution of ethyl 4-oxo-1-azabicyclo[3.3.1]non-3-yl carboxylate* (22 g, 0.104 moles) in ethanol (200 ml) was cooled in an ice bath to 5° C. and treated portionwise with sodium borohydride (4.0 g). The reaction was then allowed to warm to room temperature and stirred overnight. The solvent was then removed in vacuo, the residue partitioned between dichloromethane (200 ml) and water (75 ml) and the organic layer separated and dried (Na$_2$SO$_4$). Filtration and removal of the solvent afforded the required product as an oil (20.0 g), 85% pure by g.l.c. (OVl, 180° C.) which was used without further purification.

*J. Amer. Chem. Soc., 45, 2738 (1923) (ref. 3)

Description 5

(±) exo-1-Azabicyclo[3.3.1]nonane-3-methanol (D5)

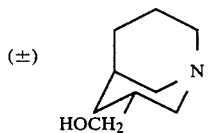

(D5)

A solution of (±) exo-methyl 1-azabicyclo[3.3.1]non-3-yl carboxylate (free base of E4 from Example 4) (2.70 g, 0.0147 mole) in dry THF (20 ml) was added dropwise to a stirred suspension of lithium aluminium hydride (1.15 g, 0.030 mole) in dry THF (80 ml) at 0° C. under nitrogen. The reaction mixture was allowed to reach room temperature over 40 minutes and then heated under reflux for 2.5 h. The mixture was cooled in an ice bath and then treated dropwise with water (1.2 ml), followed by 10% sodium hydroxide solution (3.5 ml), followed by water (1.2 ml). The inorganic solid was removed by filtration through a pad of kieselguhr, washing well with ethyl acetate, and the filtrate dried (Na$_2$SO$_4$) and concentrated to give the title compound (D5) as a yellow oil (1.80 g, 79%). This material was used without purification.

Description 6

(±) exo-1-Azabicyclo[3.2.1]octan-3-ol (D6)

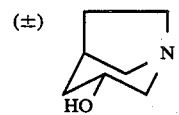

(D6)

Sodium (7.0 g) was added portionwise to a refluxing solution of 1-azabicyclo[3.2.1]octan-3-one+ (1.3 g; 0.01 moles) in ethanol (80 ml) under nitrogen over a period of 2.5 h. The reaction was refluxed until all sodium had reacted and then quenched at ice temperatuure with glacial acetic acid (25 ml). After filtration, the solution was concentration in vacuo and used in the next stage without further purification.

+D. P. Thill and H. S. Aaron, J. Org. Chem., 1968, 33, 4376 (ref. 4)

Description 7

(±) exo 3-Cyano-1-azabicyclo[3.2.1]octane (D7)

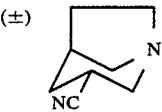

(D7)

1-Azabicyclo[3.2.1]octan-3-one* (2.7 g; 0.022 moles) in dry 1,2-dinmethoxyethane (300 ml), under nitrogen, was treated with tosylmethyl isocyanide (3.5 g; 0.029 moles) and ethanol (4.6 ml) at 0° C. Potassium t-butoxide (6.8 g, 0.06 moles) was added portionwise at such a rate as to be able to maintain the temperature between 5° C. and 10° C. The reaction mixture was allowed to warm to room temperature over 30 min., and then heated at 40° C. for a further 2.5 h. The mixture was cooled and filtered and the residue washed with 1,2-dimethoxyethane. The combined filtrates were concentrated in vacuo and the residual gum purified by column chromatography on alumina eluting with 20% methanol in ethyl acetate. The title compound (D7) was obtained as an oil (2.0 g; 66%).

*ref. 4

Ir $\nu$ (CN) 2225 cm$^{-1}$.

Description 8

(±) cis-4-Benzyl-2-oxo-2a,3,4,5,6,6a-hexahydro-7H-furo[3,4-c]pyridine (D8)

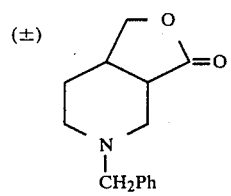

(D8)

A solution of 2-oxo-7H-furo[3,4-c]pyridine+ hydrochloride salt (9.43 g, 0.055 mole) in a mixture of ethanol (150 ml), water (30 ml) and 5M hydrochloric acid (5 ml) was hydrogenated over 5% Pt/C (400 mg) at 45° C. and 150 psi for 15 h. The catalyst was filtered off through a pad of kieselguhr and the filtrate cooncentrated in vacuo. The residue was basified with saturated potassium carbonate solution and extracted with chloroform (3×70 ml). The organic extract was dried (Na₂SO₄) and concentrated in vacuo to leave a brown oil (8.5 g), which was dissolved in dry acetone (200 ml) and treated with anhydrous potassium carbonate (16.5 g) and benzyl bromide (7.2 ml). The mixture was stirred at room temperature for 2 h, then diluted with water (400 ml) and extracted with ethyl acetate (3×150 ml). The combined extracts were dried (Na₂SO₄) and concentrated in vacuo to give a brown oil, which was chromatographed on silica gel eluting with ether to give the title compound (D8) as a pale yellow oil (3.15 g, 25%).
+J. Kuthan, L. Musil, V. Jehlicka; Collection Czechoslov. Chem. Comm., 1977, 42, 283 (ref. 5)

¹H Nmr (CDCl₃) δ:
1.52–1.65 (1H, m, 5ax) 1.77–1.86 (1H, m, 5eq) 1.95 (1H, dt, 6ax, J=2.5 Hz and J=13.5 Hz) 2.31 (1H, dd, 2ax, J=5 Hz and J=13.5 Hz) 2.42–2.52 (1H, m, 4ax) 2.59–2.65 (1H, m 3 eq) 2.66–2.73 (1H, m, 6 eq) 3.21–3.28 (1H, m, 2eq) 3.45–3.62 (2H, m, CH₂Ph) 3.96–4.02 (1H, m, 1×CH₂OCO) 4.18–4.25 (1H, m, 1×CH₂OCO) 7.20–7.34 (5H, m, PhCH₂)

Description 9

(±) exo-Ethyl 1-benzyl-1-azoniabicyclo[2.2.1]heptan-3-yl-carboxylate bromide (D9)

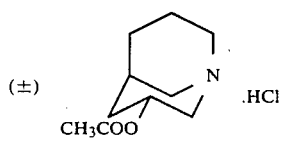

(±) cis-4-Benzyl-2-oxo-2a,3,4,5,6,6a-hexahydro-7H-furo[3,4-c]pyridine (D8, 2.80 g, 0.012 mole) was treated with a saturated solution of hydrogen bromide in ethanol (150 ml) and the mixture stirred at room temperature for 9 days. The mixture was concentrated in vacuo and the residue basified with saturated potassium carbonate soluton then extracted with chloroform (3×80 ml). The combined extracts were dried and concentrated in vacuo to give the title compound (D9) as a yellow gum (4.0 g, 98%), which was used without purification.

Example 1

(±) exo-1-Azabicyclo[3.3.1]non-3-yl acetate hydrochloride

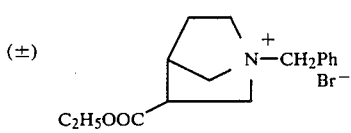

A solution of crude exo-1-azabicyclo[3.3.1]nonan-3-ol (D1) (3.0 g, 0.021 mole) in acetic anhydride (50 ml) was heated under reflux for 2.5 h. The reaction solution was then concentrated in vacuo and the residual oil dissolved in chloroform (100 ml) and washed with saturated sodium bicarbonate solution. The organic solution was dried (Na₂SO₄) and concentrated in vacuo to give a brown oil. This was chromatographed on silica gel eluting initially with chloroform increasing to 5% methanol/chloroform to remove the required product. This was further purified by distillation (b.p. 90°–100° C. at 0.2 mm Hg) and the colourless oil obtained converted to its hydrochloride salt. This was recrystallised from ethanol/ether to give the title compound a white solid (1.73 g, 37% from ketone) m.p. 188°–189° C.

Analysis: C₁₀H₁₇NO₂·HCl requires: C: 54.67%; H: 8.26%; N: 6.38%. found: C: 54.44%; H: 8.54%; N: 6.28% Nmr: (d⁶DMSO) δ: 1.60–2.30 (10H, m, 3×CH₂, CH, singlet at 2.03 for CH₃CO) 3.00–3.55 (6H, m, 3×CH₂N) 5.40–5.55 (1H, m, CHOCO) 11.60 (1H, br. s, NH) Ir: ν(C=O) 1725 cm⁻¹

Example 2

(±) exo-3-Ethoxy-1-azabicyclo[3.3.1]nonane oxalate

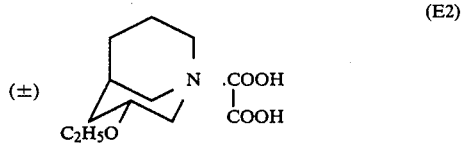

A solution exo-1-azabicyclo[3.3.1]nonan-3-ol (D1) (1.75 g, 12.4 mmol) in dichloromethane (20 ml) was cooled in an ice bath and treated with benzyl bromide (1.7 ml, 14.5 mmol). The solution was stirred for 0.5 h, diluted with dry ether (100 ml) and the white solid filtered off, washed with ether and dried. A solution of this salt in dry dimethylformamide (DMF) (25 ml) was cooled in an ice bath and treated with sodium hydride (430 mg of an 80% dispersion in oil, 14.5 mmol). The mixture was stirred for 0.5 h, treated with bromoethane (1.1 ml, 14.5 mmol) and allowed to stir at room temperature overnight. Any excess sodium hydride was destroyed by the addition of ethanol (6 ml) and the mixture then concentrated in vacuo. The residue was dissolved in ethanol (120 ml) and hydrogenated over 10% Pd/C (300 mg) at 40° C. and atmospheric pressure until the uptake of hydrogen was complete. The catalyst was filtered off and the filtrate concentrated in vacuo. The residue was dissolved in chloroform (60 ml), washed with saturated potassium carbonate solution, then dried (Na₂SO₄), filtered and evaporated to dryness. The yellow oil was chromatographed on silica gel eluting with 15% methanol/chloroform and the product distilled (b.p. 130°–140° C. at 0.5 mm Hg) to give a colourless oil. This was converted to the oxalate salt and crystallised from ethanol/ether to give the title compound as a white solid (760 mg, 24%) m.p. 133°–135° C.

Analysis: C₁₀H₁₉NO·C₂H₂O₄ requires C: 55.60%; H: 8.11%; N: 5.40% found: C: 55.63%; H: 8.47%; N: 5.40%

Nmr (d⁶DMSO) δ: 1.10 (3H, t, CH₃ CH₂, J=7 Hz) 1.55–2.25 (7H, m, 3×CH₂, CH) 2.85–3.60 (8H, m, 3×CH₂N, CH₂CH₃) 4.15–4.30 (1H, m, CHOEt)

Example 3

(±) exo-1-Azabicyclo[3.3.1]non-3-yl carbamate hydrochloride

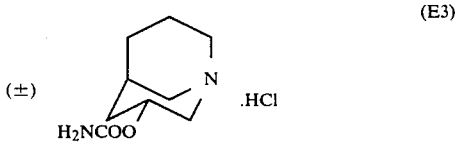

A solution of exo-1-azabicyclo[3.3.1]nonan-3-ol (D1) (4.0 g, 0.028 mole) in pyridine (10 ml) and DMF (30 ml)

at 0° C. was treated with phenylchloroformate (3.2 ml, 0.028 mole) and stirred for 0.75 h. The solution was treated with saturated sodium bicarbonate solution (60 ml) and extracted with ether (3×60 ml). The combined extracts were concentrated in vacuo and the residue stirred at room temperature with 0.88 ammonia solution (50 ml) for 0.5 h. The solution was saturated with potassium carbonate and extracted with chloroform (3×50 ml). The combined extracts were dried ($Na_2SO_4$) and concentrated in vacuo to give a yellow oil, which crystallised on standing. This was chromatographed on silica gel eluting initially with chloroform to remove the phenol present and then with methanol to remove the carbamate. The latter was crystallised from ether to give a white solid m.p. 128°–130° C., which was converted to its hydrochloride salt and recrystallised from ethanol to give the title compound as a white solid (1.10 g, 18%) m.p. 231°–233° C.

Nmr ($d^6DMSO$) δ: 1.65–2.30 (7H, m, 3×$CH_2$, CH) 2.95–3.55 (6H, m, 3×$CH_2N$) 5.25–5.40 (1H, m, CHOCO) 6.50–6.90 (2H, br.d, $NH_2$) 11.50 (1H, br.s, NH)

Example 4

(±) exo-Methyl 1-azabicyclo[3.3.1]non-3-yl carboxylate oxalate

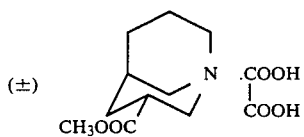

(E4)

A solution of (±)exo-3-cyano-1-azabicyclo[3.3.1]nonane (D2) (1.70 g, 0.011 mole) in concentrated hydrochloric acid (20 ml) and water (8 ml) was heated under reflux for 2.5 h and then left at room temperature overnight. The mixture was concentrated in vacuo and toluene (2×100 ml) used to azeotrope out all the water, to yield the intermediate acid (±) exo-1-azabicyclo[3.3.1]-non-3-yl carboxylic acid. The residue was dissolved in methanol (80 ml), treated with ether/HCl (20 ml) and heated under reflux for 1.5 h. The solution was evaporated in vacuo and the residue taken up in chloroform (100 ml), washed with saturated sodium bicarbonate solution, dried ($Na_2SO_4$) filtered and concentrated in vacuo. The residue was distilled (b.p. 140°–150° C. at 0.1 mm Hg) to give a colourless oil (1.40 g, 67%). This was converted to its oxalate salt and crystallised from methanol/ether to give the title compound as a white solid m.p. 101°–104° C.

Analysis: $C_{10}H_{17}NO_2 \cdot C_2H_2O_4$ requires: C: 52.75%; H: 7.01%; N: 5.13% found: C: 52.50%; H: 7.29%; N: 5.12%

Nmr ($d^6DMSO$) δ: 1.60–2.20 (7H, m, 3×$CH_2$, CH) 3.10–3.60 (7H, m, 3×$CH_2N$, CHCOO) 3.65 (3H, s, $CH_3OCO$)

Example 5

(±) exo-Methyl 1-azabicyclo[4.3.1]dec-8-yl carboxylate oxalate

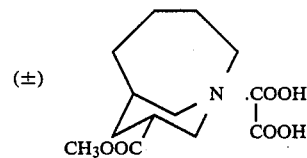

(E5)

The title compound was prepared from (±) exo-8-cyano-1-aza-bicyclo[4.3.1]decane (2.30 g, 0.014 mole) (described in EP-A-0094742) by the method of Example 4, via the intermediate acid (±) exo-1-azabicyclo[4.3.1]-dec-8-yl carboxylic acid, to give the title compound as a white solid (2.55 g, 63%) m.p. 113°–115° C.

Analysis: $C_{11}H_{19}NO_2 \cdot C_2H_2O_4 \cdot 0.5H_2O$ requires: C: 52.65%; H: 7.42%; N: 4.72% found: C: 52.57%; H: 7.41%; N: 4.58%

Nmr ($d^6DMSO$) δ: 1.45–2.30 (9H, m, 4×$CH_2$, CH) 3.05–3.40 (7H, m, 3×$CH_2N$, CHCOO) 3.66 (3H, s, $CH_3OCO$) Ir ν (C=O) 1725 cm$^{-1}$

Example 6

(±) exo-1-Azabicyclo[3.2.1]oct-6-yl acetate hydrochloride

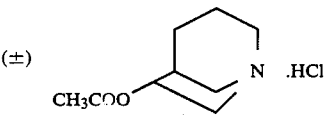

(E6)

To a stirred solution of 1-azabicyclo-[3.2.1]octan-6-one* (7.5 g, 0.06 moles) in ethanol (250 ml) was added sodium metal (20 g) in small portions at a rate which maintained reflux. The reaction was then heated at reflux until all the metal had reacted and a t.l.c. (alumina, 10% methanol/ethyl acetate) showed an absence of starting material. After cooling to 10° C. glacial acetic acid was added dropwise to the stirred mixture until pH5. The precipitated sodium acetate was filtered off and washed with ethanol. The combined filtrate was concentrated in vacuo, the residue dissolved in acetic anhydride (100 ml) and heated under reflux for 2 h. The excess acetic anhydride was removed in vacuo and the residue dissolved in chloroform. The organic solution was washed with saturated aqueous potassium carbonate, dried ($Na_2SO_4$), filtered and concentrated in vacuo to give a gum. Chromatography on alumina eluting with methanol (3%–10%)/ethyl acetate afforded both the exo and endo products.

*ref.2

The first fraction (obtained with 6% methanol/ethyl acetate) was distilled in a Kugelrohr at 140°/0.1 mm Hg to afford (±) exo 1-azabicyclo[3.2.1]oct-6-yl acetate as a colourless oil (2.9 g). A sample (0.5 g) was converted to the hydrochloride salt m.p. 151°–6°.

Analysis: $C_9H_{15}NO_2 \cdot HCl \cdot 0.25H_2O$ requires: C: 51.43%; H: 7.91%; N: 6.66% found: C: 51.22%; H: 7.99%; N: 6.75%

Nmr (free base, $CDCl_3$) δ 1.33–1.8 (4H, m, $CH_2CH_2$) 2.04 (3H, s, $OCOCH_3$) 2.1–2.2 (1H, m, CH) 2.7–2.8 (4H, m, 2×$CH_2N$) 2.85–2.95 (1H, m, CHN) 3.35 (1H, qu of d, CHN, J=14 Hz, 7 Hz, 3 Hz) 5.02 (1H, qu of d, CHOCO, J=6 Hz, 3 Hz, 1.5 Hz)

Example 7

(±) exo-Methyl 1-azabicyclo[3.2.1]oct-6-yl carboxylate hydrochloride

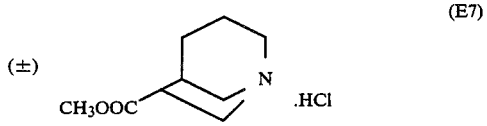

The cyanide (D3) (0.4 g, 2.9 mmoles) was dissolved in water (10 ml) and concentrated hydrochloride acid (30 ml) and heated under reflux overnight. The reaction was concentrated in vacuo and the residue, comprising the intermediate acid (±) exo-1-azabicyclo[3.2.1]oct-6-yl carboxylic acid, dissolved in methanol (20 ml) saturated with hydrogen chloride gas and heated at reflux for 1 h. After concentrating in vacuo the residual oil was dissolved in chloroform and washed with saturated aqueous potassium carbonate solution. The organic layer was dried (Na₂SO₄), filtered and evaporated in vacuo to give an oil which was distilled in a Kugelrohr b.p. 130°/1 mm Hg to afford (±) exo-methyl 1-azabicy-clo-[3.2.1]oct-6-yl carboxylate as an oil (0.26 g) which solidified on standing. Treatment with ether/HCl gave the desired product as a solid m.p. 90°–95°.

Nmr (free base, CDCl₃) δ: 1.8–2.0 (4H, m, CH₂CH₂) 2.9–3.5 (7H, m, 2×CH₂N, CHN, 2×CH) 3.75 (3H, s, CH₃O) 3.8 (1H, d of d, CHN, J=12 Hz, 5 Hz)

Example 8

(±) Methyl 1-azabicyclo[3.3.1]non-3-en-3-yl carboxylate hydrochloride

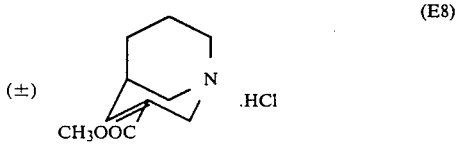

(±) Ethyl 4-hydroxy-1-azabicyclo[3.3.1]non-3-yl carboxylate (D4) (7.0 g, 0.032 moles) was treated with conc. sulphuric acid (20 ml) and glacial acetic acid (20 ml) and heated at reflux, under nitrogen for 6 h. The reaction was cooled and poured onto ice, the aqueous layer was then washed with ether and the solvents removed in vacuo. The residue, comprising the intermediate acid (±) 1-azabicyclo[3.3.1]non-3-en-3-yl carboxylic acid, was treated with methanol and heated under reflux for two days. After removal of the excess methanol in vacuo, the residual oil was basified with saturated aqueous potassium carbonate and the aqueous layer extracted with ethyl acetate (3×200 ml). After drying (Na₂SO₄), the solvent was removed in vacuo to give an oil (2.5 g) which was purified by column chromatography on silica gel eluting with 10% methanol/chloroform. The first fraction contained the desired product which was converted to its hydrochloride salt and recrystallised from ethanol/ether to give a white solid.

MS Calculated mass for C₁₀H₁₅NO₂=181.1103 Observed mass=181.1104

Nmr (CD₃OD) δ: 1.7–2.0 (4H, m, —CH₂CH₂—) 2.88–2.96 (1H, m, —CH—) 3.27–3.5 (4H, m, 2×CH₂×N) 3.8 (3H, s, —OCH₃) 3.99 (1H, d, =C—CH₂N, J=17 Hz) 4.24 (1H, d, =C—CH₂N, J=17 Hz) 7.19 (1H, d, —CH=, J=6 Hz)

Example 9

(±) exo-3-Methoxymethyl-1-azabicyclo[3.3.1]nonane oxalate salt (E9)

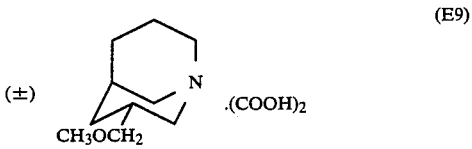

A solution of (±) exo-1-azabicyclo[3.3.1]nonane-3-methanol (D5) (1.24 g, 0.0080 mole) in dichloromethane (20 ml) at 0° C. was treated with benzyl bromide (1.1 ml, 0.0095 mole) and stirred for 40 minutes. The solution was then diluted with ether (100 ml) and a thick gum precipitated out. The mixture was allowed to stand for 15 minutes, the solvent was decanted off, the gum washed with ether (100 ml) and the solvent again decanted off. The gum was dissolved in dry DMF (100 ml) at 0° C. and the solution treated with sodium hydride (360 mg of 80% oil dispersion, 0.012 mole) and then stirred at room temperature for 30 minutes, before adding iodomethane (2.0 ml, 0.032 mole). The mixture was stirred at room temperature for 2.5 h and then concentrated in vacuo to leave a yellow semi-solid, which was dissolved in ethanol (100 ml) and hydrogenated over 10% Pd/C (400 mg) at room temperature and pressure until uptake of hydrogen ceased. The catalyst was filtered off through a pad of kieselguhr and the filtrate concentrated in vacuo to leave a beige solid, which was basified with saturated potassium carbonate solution and extracted with chloroform (3×70 ml). The combined extracts were dried (Na₂SO₄) and concentrated in vacuo to leave a yellow oil;, which was distilled in a Kugelröhr apparatus (b.p. approx. 100°–120° C. at 0.1 mm) to give a colourless oil. This was converted to its oxalate salt and crystallised from methanol/ether to give the title compound (E9) as a white solid (430 mg, 21%) m.p. 142°–143° C.

Oxalate:- ¹H Nmr (d⁶DMSO) δ: 1.45–1.60 (1H, m) 1.65–1.90 (4H, m) 2.05–2.25 (2H, m) 2.60–2.75 (1H, m, CHCH₂O) 2.95–3.45 (8H, m, 3×CH₂N, CH₂O) 3.25 (3H, s, CH₃O)

Analysis: C₁₀H₁₀NO·C₂H₂O₄ requires: C: 55.58; H: 8.16; N: 5.40% found: C: 55.60; H: 8.24; N: 5.32% M.S.: Calculated mass for C₁₀H₁₉NO=169.1467 Observed mass=169.1466

Example 10

(±) exo-Propargyl 1-azabicyclo[3.3.1]non-3-yl-carboxylate oxylate salt (E10)

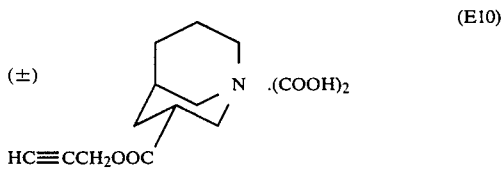

A solution of (±)-exo-3-cyano-1-azibicyclo[3.3.1]nonane (D2) (1.80 g, 0.012 mole) in 8M hydrochloric acid was heated under reflux for 2 h. The solution was concentrated in vacuo to leave a beige solid, which was treated with propargyl alcohol (30 ml) and saturated ether/HCl (0.2 ml) and the solution stirred at room temperature for 7 days. The reaction mixture was concentrated in vacuo and the residue taken up in dichloromethane (100 ml), washed with saturated sodium hydrogen carbonate solution, dried (Na2SO4) and concentrated. The residue was chromatographed on silica gel eluting with 20% methanol/ethyl acetate and the required product then distilled on a Kugelröhr apparatus (b.p. approx. 180°–190° C. at 0.2 mm) to give a colourless oil. This was converted to its oxalate salt and recrystallised from acetone/ether to give the title compound (E10) as a white solid (650 mg, 18%) m.p. 116°–118° C.

Oxalate:- $^1$H Nmr (d$^6$DMSO) δ: 1.60–2.20 (7H, m, 3×CH2, CH) 2.50 (1H, t, C≡CH, J=2.5 Hz) 3.10–3.60 (7H, m, 3×CH2N, CHCOO) 4.75 (2H, d, CH2OCO, J=2.5 Hz)

M.S.: Calculated mass for $C_{12}H_{17}NO_2$=207.1259 Observed mass=207.1258

Example 11

(±) exo-1-Azabicyclo[3.3.1]non-3-yl-N-methylcarbamate hydrochloride salt (E11)

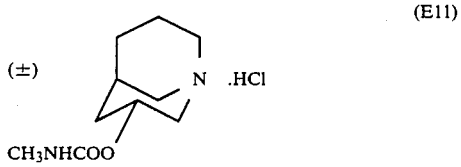

A solution of exo-1-azabicyclo[3.3.1]nonan-3-ol (D1) (2.30 g, 0.016 mole) in dry DMF (25 ml) and dry pyridine (12 ml) at 0° C. was treated with phenyl chloroformate (2.0 ml, 0.016 mole) and stirred for 0.5 h. The solution was treated with saturated sodium hydrogen carbonate solution (60 ml) and extracted with ether (3×70 ml). The combined extracts were dried (Na2SO4) and concentrated in vacuo and the residue taken up in methanol (10 ml) and treated with 25% aqueous methylamine solution (15 ml). The solution was stirred for 10 minutes, then saturated with potassium carbonate and extracted with chloroform (3×30 ml). The combined extracts were dried (Na2SO4) and concentrated in vacuo to leave an orange oil, which was chromatographed on silica gel eluting initially with chloroform to remove the phenol present, then with 15% methanol/chloroform to remove the carbamate. This was converted to its hydrochloride salt and recrystallised from methanol/ether to give the title compound (E11) as a white solid (430 mg, 11%) m.p. 201°–204° C.

Hydrochloride:-$^1$H Nmr (d$^6$DMSO)δ: 1.65–1.95 (5H, m) 2.02–2.15 (1H, m) 2.20–2.30 (1H, m) 2.57 (3H, d, CH3NH, J=5 Hz) 2.95–3.55 (6H, m, 3×CH2N) 5.25–5.40 (1H, m, CHOCO) 7.15 (1H, br.d, NHCH3)

M.S.:-Calculated mass for $C_{10}H_{18}N_2O_2$=198.1368 Observed mass=198.1360

Example 12

(±) exo-1-Azabicyclo[2.2.1]hept-3-yl acetate oxalate salt (E12)

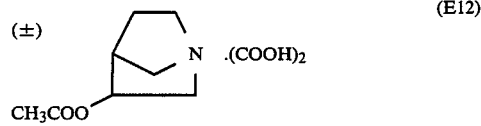

A solution of exo-1-azabicyclo[2.2.1]heptan-3-ol+ (440 mg, 3.89 mmol) in chloroform (50 ml) was treated with 130 mg of 4-dimethylaminopyridine and acetic anhydride (3 ml) and stirred at room temperature. When thin layer chromatography indicated that reaction was complete, the solution was evaporated under reduced pressure and the residue treated with excess ice-cold saturated aqueous potassium carbonate solution and extracted with chloroform. The chloroform extract was dried (Na2SO4), filtered, and evaporated to give a residue which was adsorbed from chloroform on silica gel. Elution with chloroform containing progressively increasing amounts of methanol (up to 5%) gave a product which was dissolved in ether and converted to its oxalate salt. The latter was recrystallised from ether to give the title compound (E12) (0.39 g, 41%), m.p. 117°–118°.

+D. O. Spry and H. S. Aaron, J. Org. Chem., 1969, 34, 3674 (ref. 6) K. Hasse and A. Wieland, Chem. Ber., 1960, 93, 1686 (ref. 7)

Analysis: $C_8H_{13}NO_2·C_2H_2O_4$ requires: C: 48.98; H: 6.17; N: 5.71% found: C: 48.97; H: 6.42; N: 5.69%

Nmr (CD3OD)δ: 1.65–1.77 and 2.10–2.22 (2H, m, CH2) 2.06 (3H, s, OCOCH3) 2.90–3.70 (7H, m, 3×CH2N+CH) CHO obscured by CD3OH signal

Example 13

(±) exo-3-Ethoxy-1-azabicyclo[2.2.1]heptane oxalate salt (E13)

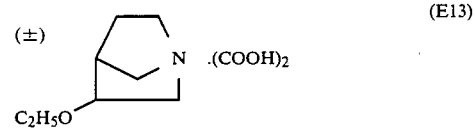

exo-1-Azabicyclo[2.2.1]heptan-3-ol+ was converted to the title compound (E13, 10%) by a method analogous to that described for E2, omitting the distillation stage. It was obtained as a hygroscopic oxalate salt.

$^1$H Nmr (d$^6$-DMSO)δ: 1.11 (3H, t, CH3CH2, J=7 Hz) 1.35–1.50 and 1.88–2.00 (2H, m, CH2) 2.85–3.60 (9H, m, 3×CH2N, CH2CH3, CH) 3.75 (1H, m, CHOEt)

M.S.: Calculated mass for $C_8H_{15}NO$=141.1154 Observed mass=141.1154

+ref. 6, ref. 7

Example 14

(±) exo-1-Azabicyclo[3.2.1]oct-3-yl acetate hydrochloride salt (E14)

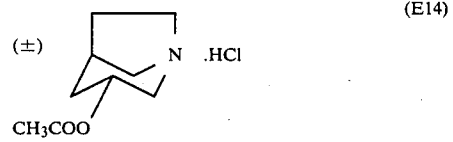

(±) exo-1-Azabicyclo[3.2.1]octan-3-ol (D6) (1 g) was refluxed with acetic anhydride (25 ml) for 3 h. After concentration in vacuo the residue was dissolved in water (50 ml), acidified with dilute hydrochloric acid and washed with ether. The aqueous phase was basified with potassium carbonate and extracted into chloroform (3×50 ml). Drying (Na$_2$SO$_4$) followed by evaporation of solvent afforded a brown oil (0.7 g) which was distilled (130° C./0.1 mmHg) and converted into the hydrochloride salt. Purity was found to be 75% by $^1$H Nmr and the signals ascribed to the title compound (E14) are indicated below.

Hydrochloride:-$^1$H Nmr (d$^6$-DMSO)δ: 1.60–2.20 (4H, m) 2.06 (3H, s) 2.70 (1H, m) 3.00–3.60 (6H, m) 5.15 (1H, m)

Example 15

(±) exo-Methyl-1-azabicyclo[3.2.1]oct-3-yl carboxylate hydrochloride (E15)

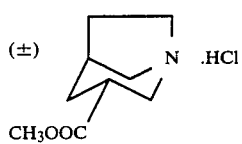

(±) exo-3-Cyano-1-azabicyclo[3.2.1]octane (D7) (1.0 g, 7.4 mmoles) was refluxed in 9M hydrochloric acid (30 ml) for 5 h. The solution was evaporated to dryness and the residue was refluxed for 3 h in methanol—HCl. After concentration in vacuo the residue was dissolved in water (40 ml), acidified with dilute hydrochloric acid and washed with ether. The aqueous phase was saturated with potassium carbonate and extracted into chloroform (3×50 ml). After drying (Na$_2$SO$_4$), evaporation of solvent afforded a brown oil (0.8 g, 65%) which was converted to the title compound (E15) as the hydrochloride salt (m.p. 184.5°–185° C. from methanol-ether).

Hydrochloride: $^1$H Nmr (d$^6$-DMSO)δ: 1.70–2.00 (3H, m) 2.00–2.20 (1H, m) 2.65 (1H, m) 3.00–3.50 (7H, m) 3.65 (3H, s)

$^{13}$C Nmr (d$^6$-DMSO) δ: 26.48, 31.01, 32.64, 33.08, 49.77, 51.91, 51.94, 56.88, 171.90.

Analysis: C$_9$H$_{15}$NO$_2$·HCl requires: C: 52.56 H: 7.84 N: 6.81 found: C: 52.09 H: 7.87 N: 6.81

Example 16

(±) exo-Methyl 1-azabicyclo[2.2.1]hept-3-yl carboxylate oxalate salt (E16)

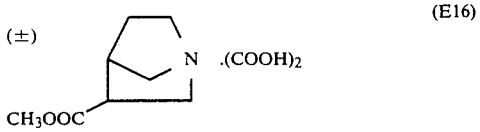

A solution of (±) exo-ethyl 1-benzyl-1-azoniabicyclo[2.2.1]-heptan-3-ylcarboxylate bromide (D9, 4.0 g, 0.012 mole) in ethanol (150 ml) plus glacial acetic acid (2 ml) was hydrogenated over 10% Pd/C (500 mg) at atmospheric pressure and 40° C. until uptake of hydrogen ceased. The catalyst was filtered off through a pad of kieselguhr and the filtrate concentrated in vacuo to leave a beige semi-solid, which was treated with 8M hydrochloric acid (70 ml) and heated under reflux for 2 h. The solution was concentrated in vacuo to give a beige solid (comprising the intermediate acid (±) exo-1-azabicyclo[2.2.1]hept-3-yl carboxylic acid), which was treated with methanolic hydrogen chloride (100 ml) and heated under reflux for 30 minutes followed by 2 days at room temperature. The solution was concentrated in vacuo and the residue basified with saturated sodium hydrogen carbonate solution, then extracted with chloroform (3×60 ml). The combined extracts were dried (Na$_2$SO$_4$) and concentrated to give an orange oil, which was distilled in a Kugelröhr apparatus (b.p. approx. 110°–120° C. at 0.4 mm) to give a colourless oil (1.3 g, 70%). A portion of this material was converted to its oxalate salt and recrystallised from methanol/ether to give the title compound (E16) as a white solid, m.p. 134°–136° C.

Oxalate:-$^1$H Nmr (d$^6$DMSO)δ: 1.65–1.75 (1H, m) 1.90–2.05 (1H, m) 2.85–2.95 (1H, m) 2.95–3.15 (4H, m) 3.22–3.32 (1H, m) 3.35–3.50 (2H, m) 3.68 (3H, s, COOCH$_3$)

Analysis: C$_8$H$_{13}$NO$_2$·C$_2$H$_2$O$_4$ requires: C: 48.98; H: 6.12; N: 5.71% found: C: 48.97; H: 6.17; N: 5.51%

M.S.: Calculated mass for C$_8$H$_{13}$NO$_2$=155.0946 Observed mass=155.0946

Example 17

(±) exo-1-Azabicyclo[3.2.1]oct-6-yl propionate hydrochloride (E17)

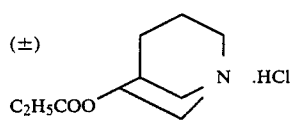

A solution of (±)-exo-1-azabicyclo[3.2.1]oct-6-yl acetate (E6) (0.3 g, 0.00165 mole) in methanol (50 ml) was saturated with HCl gas and then heated under reflux for 1 h. The solution was then concentrated in vacuo to a gum which was dissolved in chloroform (25 ml) and treated with propionyl chloride (10 ml) under reflux for 1 h. The solvent and excess propionyl chloride were removed in vacuo and the residue redissolved in chloroform. The organic solution was then washed with aqueous saturated potassium carbonate solution, dried (Na$_2$SO$_4$) and concentrated in vacuo to a gum. The residue was distilled in a Kugelröhr at 0.1 mm and 150° C. to afford (±)-exo-1-azabicyclo[3.2.1]oct-6-yl propionate (0.29 g, 97%) as a colourless oil.

The hydrochloride was prepared by dissolving the free base in ether and adding an excess of ether saturated with hydrogen chloride. The salt immediately precipitated out and was collected by filtration to afford the title compound (E17), m.p. 155°–160° C.

Hydrochloride: $^1$H Nmr, (d$^6$-DMSO)δ: 1.05 (3H, t, J=6.5 Hz, CH$_3$) 1.55–1.87 (4H, m, 3-CH$_2$, 4-CH$_2$) 2.275 (1H, m, 5-CH) 2.35 (2H, q, J=6.5 Hz, COCH$_2$) 2.95–3.35 (5H, m, 2-CH$_2$, 7-CH, 8-CH$_2$) 3.89 (1H, d,d, J=13.5 Hz and 6.8 Hz, 7-CH) 5.09 (1H, d,d, J=2.7 Hz and 6 Hz, 6-CH)

Example 18

(±) exo-6-n-Propoxy-1-azabicyclo[3.2.1]octane hydrochloride (E18)

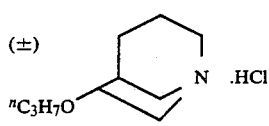

A solution of (±)-exo-1-azabicyclo[3.2.1]oct-6-yl acetate (E6) (0.75 g, 0.0044 mole) was dissolved in ether and treated with benzyl bromide (0.75 g, 0.0044 mole) for 2 h at 20° C. The reaction mixture was then concentrated in vacuo to a gummy solid which was dissolved in water (10 ml) and concentrated hydrochloric acid (5 ml) and heated to reflux for 2 h. The reaction mixture was then concentrated in vacuo to a gum and held at 50° C. in high vacuo for 16 h. This gum was dissolved in dry dimethylformamide (20 ml) and treated with n-propyl bromide (1 g, 0.0082 mole) and an 80% oil dispersion of sodium hydride (260 mg, 0.0135 mole) at 20° C. with continuous stirring for 2 days. Acetic acid (1 ml) was then added dropwise and the rection mixture concentrated in vacuo to a gum. The residue was taken up in methanol (50 ml) and hydrogenated at atmospheric pressure over 10% Pd/C. The reaction mixture was then filtered through Kieselguhr and concentrated in vacuo to a gum which was dissolved in chloroform and washed with saturated aqueous potassium carbonate solution. The organic phase was dried (Na₂SO₄) and concentrated in vacuo to a gum. This was distilled in Kugelröhr at 0.1 mm and 170° C. to afford (±)-exo-6-n-propoxy-1-azabicyclo[3.2.1]octane (0.36 g, 48%) as a colourless oil.

$^1$H Nmr (CDCl$_3$)δ: 0.91 (3H, t, J=7 Hz, CH$_3$) 1.24–1.68 (6H, m, 3-CH$_2$, 4-CH$_2$, OCH$_2$CH$_2$) 2.13 (1H, q, J=3 Hz, 5-H) 2.64–2.96 (5H, m, 2-CH$_2$, 8-CH$_2$, 7 C-H) 3.20 (1H, d,d, d, J=2 Hz, 4 Hz and 13 Hz, 7-H) 3.34 and 3.38 (2H, each t, J=6.6 Hz, O-CH$_2$) 3.80 (1H, d,d, d, J=1 Hz, 2.5 Hz and 4.5 Hz, 6-H)

The hydrochloride salt (E18) was obtained as a very hygroscopic powder by the procedure described in example 17.

Example 19

(±) exo-6-Ethoxy-1-azabicycl9[3.2.1]octane hydrochloride (E19)

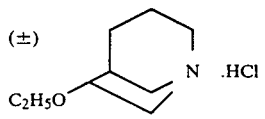

A solution of (±)-exo-1-azabicyclo[3.2.1]oct-6-yl acetate (E6) (1 g, 0.0059 mole) in diethyl ether (20 ml) was treated with benzyl bromide (1 g, 0.0059 mole) for 16 h at 20° C. The precipitated quaternary salt (2 g, 0.0059 mole) was collected by filtration and (1.5 g, 0.045 mole) of this highly deliquescent powder dissolved in water (20 ml). To this was added concentrated hydrochloric acid (10 ml) and the solution was heated under reflux for 2.5 h. The reaction mixture was then concentrated in vacuo to a gum and held at 50° C. in high vacuo for 16 h. This gum was dissolved in dry dimethyl formamide (20 ml) and treated with ethyl bromide (0.5 g, 0.0046 mole) and an 80% oil dispersion of sodium hydride (138 mg, 0.0046 mole) at 20° C. with stirring for 1 day. To this reaction mixture was then added a further portion of ethyl bromide (0.5 g, 0.0046 mole) and 80% oil dispersion of sodium hydride (138 mg, 0.0046 mole) and the reaction stirred at 20° C. for a further day. Acetic acid (1 ml) was then added dropwise to the reaction mixture and solvent removed in vacuo. The residue was dissolved in methanol (50 ml) and hydrogenated over 10% Pd/C at atmospheric pressure. The reaction was then filtered through Kieselguhr and concentrated in vacuo to a gum. This was dissolved in chloroform and washed with an aqueous saturated solution of potassium carbonate. The organic phase was dried (Na₂SO₄) and concentrated in vacuo to a gum which was distilled in a Kugelröhr at 0.1 mm and 100°–120° C. to afford (±)-exo-6-ethoxyl-1-azabicyclo[3.2.1]octane (0.4 g, 58%) as a colourless oil.

$^1$H Nmr (CDCl$_3$) δ: 1.19 (3H, t, j=6.6 Hz, CH$_3$) 1.25–1.70 (4H, m, 3-CH$_2$, 4-CH$_2$) 2.13 (1H, q, J=2.5 Hz, 5-CH) 2.60–2.95 (5H, m, 2-CH$_2$, 8-CH$_2$, 7-CH) 3.20 (1H, d, d, d, J=2.5 Hz, 4.4 Hz and 13.2 Hz, 7-H) 3.44 and 3.45 (2H, each q, J=6.6 Hz, 0-CH$_2$) 3.82 (1H, d, d, d, J=1 Hz, 2.5 Hz and 4.4 Hz, 6-H)

The hydrochloride salt (E19) was prepared by treating a solution of the free base in ether with ether saturated with hydrogen chloride. The product which immediately crystallised out was collected by trituration but was too hygroscopic for satisfactory analytical data to be obtained.

Example 20

(±) exo-1-Azabicyclo[3.2.1]oct-6-yl-N-methylcarbamate oxalate salt (E20)

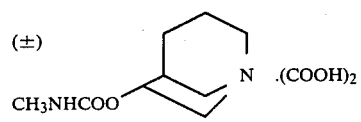

A solution of (±)-exo-1-azabicyclo[3.2.1]oct-6-yl acetate (E6) (0.75 g, 0.0044 mole) in ether was treated with benzyl bromide (0.75 g, 0.0044 mole) for 2 h at 20° C. The reaction mixture was then concentrated in vacuo to a gummy solid which was dissolved in water (10 ml) and concentrated hydrochloric acid (5 ml) and heated to reflux for 2 h. The reaction mixture was then concentrated in vacuo to a gum and held at 50° C. in high vacuo for 16 h. This gum was dissolved in dry dimethyl formamide (10 ml) and pyridine (5 ml) and treated with phenyl chloroformate (1.4 g, 0.009 mole) dropwise at 0° C. The reaction was allowed to warm to room temperature over 30 min and then treated with an excess of dimethyl formamide saturated with methylamine gas and allowed to stand at room temperature for 1 h. The solvents were then removed in vacuo and the residue dissolved in chloroform. The organic phase was washed with aqueous saturated potassium carbonate solution dried (Na₂SO₄) and concentrated in vacuo to a gum. Chromatography on alumina in a gradient of 25–35% methanol in ethyl acetate yielded (±)-exo-1-azabicyclo[3.2.1]oct-6-yl-N-methylcarbamate (0.44 g, 0.0024 mole) as a colourless oil.

The free base (440 mg, 0.0024 mole) in ether was treated with oxalic acid (200 mg, 0.0022 mole) in methanol (1 ml) and the white solid which immediately precipitated collected by filtration to afford the title compound (E20), m.p. 160°-162° C.

Oxalate: ¹H Nmr (CD₃OD) δ: 1.73-1.95 (4H, m, 3-CH₂, 4-CH₂) 2.60 (1H, m, 5-CH) 2.70 (3H, s, NHCH₃) 3.25-3.55 (5H, m, 2-CH₂, 8-CH₂, 7-CH) 3.90 (1H, d, d, J=5 Hz, 13 Hz, 7-CH) 5.10 (1H, d, d, J=2.5 Hz, 12 Hz, 6-H)

Analysis: C₉H₁₆N₂O₂.C₂H₂O₄ requires: C: 48.17; H: 6.62; N: 10.21% found: C: 48.04; H: 6.75; N: 10.4%

Example 21

(±) exo-1-Azabicyclo[3.3.1]non-3-yl propionate hydrochloride salt (E21)

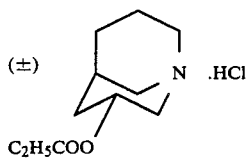

(E21)

exo-1-Azabicyclo[3.3.1]nonan-3-ol (D1) (2.50 g, 0.018 mole) was treated as in the method of Example 1, but using propionic anhydride in place of acetic anhydride. A colourless oil was obtained after distillation (b.p. 140°-50° C. at 0.1 mm), which was converted to its hydrochloride salt and recrystallised from ethanol/ether to give the title compound (E21) as a white solid (780 mg, 19%) m.p. 180°-183° C.

Hydrochloride: ¹H Nmr (d⁶-DMSO) δ: 1.05 (3H, t, CH₃CH₂, J=7 HZ) 1.65-1.95 (5H, m) 2.05-2.15 (1H, m) 2.22-2.28 (1H, m) 2.34 (2H, q, CH₂CH₃, J=7 Hz) 3.05-3.40 (5H, m) 3.45-3.55 (1H, m) 5.45-5.57 (1H, m, CHOCO)

M.S.: Calculated mass for C₁₁H₁₉NO₂=197.1416 Observed mass=197.1420

Example 22

(±) exo-3-Methoxy-1-azabicyclo[3.3.1]nonane oxalate salt (E22)

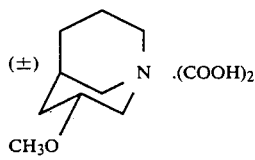

(E22)

exo-1-Azabicyclo[3.3.1]nonan-3-ol (D1)(1.04 g, 0.0074 mole) was treated as in the method of Example 2, except that iodomethane was used in place of bromoethane. A colourless oil was obtained after distillation (b.p. 100°-120° C. at 0.2 mm), which was converted to its oxalate salt and recrystallised from methanol/ether to give the title compound (E22) as a white solid (180 mg, 10%) m.p. 118°-120° C.

Oxalate: ¹H Nmr (d⁶-DMSO) δ: 1.55-2.00 (5H, m) 2.10-2.25 (2H, m) 2.85-2.95 (1H, m) 3.05-3.35 (4H, m) 3.32 (3H, s, CH₃O) 3.50-3.65 (1H, m) 4.10-4.20 (1H, m, CHOMe)

Analysis: C₉H₁₇NO.C₂H₂O₄ requires: C: 53.87; H: 7.81; N: 5.71% found: C: 53.72; H: 7.91; N: 5.64%

M.S.: Calculated mass for C₉H₁₇NO=155.1310 Observed mass=155.1316

Example 23

(±) exo-3-n-Propoxy-1-azabicyclo[3.3.1]nonane oxalate salt (E 23)

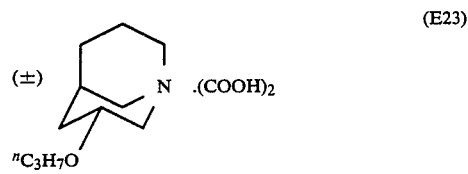

(E23)

exo-1-Azabicyclo[3.3.1]nonan-3-ol (D1) (2.03 g, 0.0144 mole) was treated as in the method of Example 2, except that 1-bromopropane was used in place of bromoethane and the alkylation step was carried out at 60° C. over 15 h. A colourless oil was obtained after distillation (b.p. approx. 150° C. at 0.2 mm), which was converted to its oxalate salt and recrystallised from ethanol/ether to give the title compound (E23) as a white solid (1.80 g, 46%) m.p. 88°-90° C.

Oxalate: ¹H-Nmr (d⁶-DMSO) δ: 0.85 (3H, t, CH₂CH₂CH₃ J=7 Hz) 1.42-1.55 (2H, m, CH₂CH₂CH₃) 1.55-2.00 (5H, m) 2.08-2.25 (2H, m) 2.85-2.97 (1H, m) 3.05-3.35 (4H, m) 3.35-3.50 (2H, m, CH₂CH₂CH₃) 3.50-3.60 (1H, m) 4.15-4.30 (1H, m, CHOPr)

M.S.: Calculated mass for C₁₁H₂₁NO=183.1623 Observed mass=183.1623

Example 24

(±) exo-1-Azabicyclo[3.3.1]non-3-yl-N,N-dimetnyl-carbamate hydrochloride (E24)

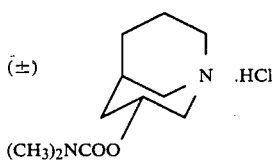

(E24)

exo-1-Azabicyclo[3.3.1]nonan-3-ol (D1) (1.72 g, 0.012 mole) was treated as in the method of Example 11, but using an aqueous dimethylamine solution in place of methylamine solution. The pale yellow oil obtained after column chromatography was converted to its hydrochloride salt and recrystallised from methanol/ether to give the title compound (E24) as a white solid (490 mg, 16%) m.p. 260°-265° C. dec.

Hydrochloride: ¹H Nmr (d⁶-DMSO) δ: 1.60-1.95 (5H, m) 2.05-2.17 (1H, m) 2.20-2.30 (1H, m) 2.80 (6H, br.s, (CH₃)₂N) 3.05-3.60 (6H, m, 3×CH₂N) 5.25-5.42 (1H, m, CHOCO)

M.S.: Calculated mass for C₁₁H₂₀N₂O₂=212.1525 Observed mass=212.1503

Example 25

(±) exo-Ethyl 1-azabicyclo[3.3.1]non-3yl carboxylate oxalate salt (E25)

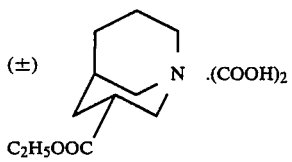

(E25)

exo-3-Cyano-1-azabicyclo[3.3.1]nonane (D2) (700 mg, 0.0047 mole) was treated as in the method of Example 4, but using ethanol instead of methanol in the esterification step. The colourless oil obtained on distillation (b.p. approx. 150°-160° C. at 0.1 mm) was converted to its oxalate salt and recrystallised from ethanol/ether to give the title compound (E25) as a white solid (370 mg, 28%) m.p. 84°-85° C.

Oxalate: $^1$H Nmr (d$^6$-DMSO) δ: 1.21 (3H, t, CH$_2$CH$_3$, J=7 Hz) 1.65-1.94 (4H, m) 2.02-2.20 (3H, m) 3.10-3.20 (2H, m) 3.24-3.40 (3H, m) 3.44-3.55 (2H, m) 4.11 (2H, q, CH$_2$CH$_3$, J=7 Hz)

M.S.: Calculated mass for C$_{11}$H$_{19}$NO$_2$ = 197.1416 Observed mass = 197.1415

Biological Activity

Radio ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H—OXO—M) experiments. For 3H-Quinuclidinyl Benzilate (3H—QNB), 1 ml of stored membranes is diluted to 30 ml and 0.1 ml mixed with test compound and 0.27 nM (c. 25,000 cpm) 3H—QNB (Amersham International). For 3H—OXO—M, 1 ml of membranes is diluted to 6 ml and 0.1 ml mixed with test compound and 2 nM (c. 25,000 cpm) 3H—OXO—M (New England Nuclear).

Non-specific binding of 3H—QNB is defined using 1 μM Atropine sulphate (2 μM Atropine) and of 3H—OXO—M using 10 μM Oxotremorine. Non-specific binding values typically are 5% and 25% of total binding, respectively. Incubations are carried out at 37° C. for 30 min and the samples filtered using Whatman GF/B filters. (In the 3H—OXO—M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarinic agonist 3H—OXO—M and the muscarinic antagonist 3H—QNB. The ratio IC$_{50}$(3H—QNB)/IC$_{50}$(3H—OXO—M) gives an indication of the compound. Agonists typically exhibit a large ratio; antagonists typically exhibit a ratio near to unity. The results are shown in Table 1.

TABLE 1

| Compound | [3H]—OXO—M IC$_{50}$ (nM) | [3H]—QNB IC$_{50}$ (nM) |
|---|---|---|
| E1 | 81 | 3900 |
| E2 | 210 | 6500 |
| E3 | 103 | 36000 |
| E4 | 81 | 3900 |
| E5 | 153 | 3200 |
| E6 | 82 | 27000 |
| E7 | 510 | 65000 |
| E8 | 118 | 4100 |
| E9 | 1300 | 38000 |
| E10 | 40 | 510 |
| E11 | 460 | 5200 |
| E12 | 175 | 46000 |
| E13 | 510 | 54000 |
| E14 | 38 | 14000 |
| E15 | 80 | 11000 |
| E16 | 190 | 60000 |
| E17 | 410 | 7300 |
| E18 | 630 | 15500 |
| E19 | 460 | 64000 |
| E20 | 1900 | 42000 |
| E21 | 367 | 1000 |
| E22 | 5000 | 170000 |
| E23 | 160 | 1200 |
| E24 | 255 | 1800 |
| E25 | 65 | 620 |

What is claimed is:

1. A compound of formula (I) or a pharmaceutically acceptable salt thereof:

in which A represents a bond or —CH$_2$— and B represents hydrogen, or A and B together with the carbon atom to which they are both attached represents a group

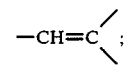

R represents R$_1$OOC— in which R$_1$ is C$_{1-4}$ alkyl, C$_{2-4}$ alkenyl or C$_{2-4}$ alkynyl; R$_2$O— in which R$_2$ is C$_{1-3}$ alkyl, C$_{1-2}$ alkylcarbonyl or aminocarbonyl optionally substituted by one or two methyl groups; or R$_3$CH$_2$— in which R$_3$ is C$_{1-2}$ alkoxy; and p represents an integer of 2 to 4, and wherein compounds of formula (I) where B is hydrogen have the stereochemical configuration in which the group R and the methylene bridge are both on the same side of the plane of the molecule which contains both bridge head atoms and the ring carbon atom bonded to the group R.

2. A compound according to claim 1, wherein A is a bond or —CH$_2$— and B is hydrogen.

3. A compound according to claim 1, wherein p is 2 or 3.

4. A compound according claim 1, wherein R is methoxycarbonyl, ethoxycarbonyl, prop-2-ynyloxycarbonyl, methoxy, ethoxy, n-propoxy, methylcarbonyloxy, ethylcarbonyloxy, aminocarbonyloxy, methylaminocarbonyloxy, dimethylaminocarbonyloxy or methoxymethyl.

5.
- (±) exo-1-Azabicyclo[3.3.1]non-3-yl acetate,
- (±) exo-3-ethoxy-1-azabicyclo[3.3.1]nonane,
- (±) exo-1-azabicyclo[3.3.1]non-3-yl carbamate,
- (±) exo-methyl 1-azabicyclo[3.3.1]non-3-yl carboxylate,
- (±) exo-methyl 1-azabicyclo[4.3.1]dec-8-yl carboxylate,
- (±) exo-1-azabicyclo[3.2.1]oct-6-yl acetate ,
- (±) exo-methyl 1-azabicyclo[3.2.1]oct-6-yl carboxylate,
- (±) exo-methyl 1-azabicyclo[3.3.1]non-3en-3-yl carboxylate,
- (±) exo-3-methoxymethyl-1azabicyclo[3.3.1]nonane,
- (±) exo-propargyl 1-azabicyclo[3.3.1]non-3-yl-carboxylate
- (±) exo-1-azabicyclo[3.3.1]non-3-yl-N-methylcarbamate,
- (±) exo-1-azabicyclo[2.2.1]hept-3yl acetate,
- (±) exo-3ethoxy-1azabicyclo[2.2.1]heptane,
- (±) exo-1-azabicyclo[3.2.1]oct-3-yl-acetate,
- (±) exo-methyl-1-azabicyclo[3.2.1]oct-3-yl carboxylate,
- (±) exo-methyl 1-azabicyclo[2.2.1]hept-3-yl carboxylate,
- (±) exo-1-azabicyclo[3.2.1]oct-6-yl propionate,
- (±) exo-6-propoxy-1-azabicyclo[3.2.1]octane,
- (±) exo-6-ethoxy-1-azabicyclo[3.2.1]octane,
- (±) exo-1-azabicyclo[3.2.1]oct-6-yl-N-methylcarbamate,
- (±) exo-1-azabicyclo[3.3.1]non-3-yl propionate,
- (±) exo-3-methoxy-1azabicyclo[3.3.1]nonane,
- (±) exo-3-n-propoxy-1-azabicyclo[3.3.1]nonane,
- (±) exo-1-azabicyclo[3.3.1]non-3-yl-N,N-dimethylcarbamate or
- (±) exo-ethyl 1-azabicyclo[3.3.1]non-3-yl carboxylate, or a pharmaceutically acceptable salt thereof.

6. A pharmaceutical composition for the treatment of dementia in mammals including humans, which comprises a therapeutically effective amount of a compound according to claim 1 and a pharmaceutically acceptable carrier.

7. A method of treatment and/or prophylaxis of dementia in mammals including humans, which comprises administering to the sufferer an effective amount of a compound according to claim 1.

* * * * *

UNITED STATES PATENT AND TRADEMARK OFFICE
CERTIFICATE OF CORRECTION

PATENT NO. : 4,870,081
DATED : September 26, 1989
INVENTOR(S) : Orlek et al.

It is certified that error appears in the above-identified patent and that said Letters Patent is hereby corrected as shown below:

```
Claim 5, col. 27, line 16, delete "exo", and
                   "3en" should be -- 3-en --;
           line 18, "laza" should be -- 1-aza --;
           line 25, "3ethoxy-lazabicyclo" should
be -- 3-ethoxy-1-azabicyclo --;
      col. 28, line 6, after "6-" insert -- n --; and
           line 11, "-lazabicyclo" should be --
-1-azabicyclo.
```

Signed and Sealed this

Twelfth Day of November, 1991

*Attest:*

HARRY F. MANBECK, JR.

*Attesting Officer*     *Commissioner of Patents and Trademarks*